United States Patent [19]

Tsay et al.

[11] Patent Number: 4,618,485

[45] Date of Patent: * Oct. 21, 1986

[54] KINETIC RADIOIMMUNOASSAY TEST METHOD AND DEVICE

[75] Inventors: Yuh-Geng Tsay, San Jose; Vipin D. Shah, Saratoga, both of Calif.

[73] Assignee: International Immunoassay Laboratories, Inc., Santa Clara, Calif.

[*] Notice: The portion of the term of this patent subsequent to Sep. 21, 2001 has been disclaimed.

[21] Appl. No.: 357,399

[22] Filed: Mar. 12, 1982

[51] Int. Cl.$^4$ ...................... G01N 33/56; G01N 33/78
[52] U.S. Cl. ....................................... 424/1.1; 436/500; 436/504; 436/517; 436/518; 436/542; 436/804
[58] Field of Search .............................. 424/1, 1.5, 1.1; 23/230 B; 436/500, 501, 504, 517, 518, 542, 804

[56] References Cited

U.S. PATENT DOCUMENTS

| | | | |
|---|---|---|---|
| 3,966,897 | 6/1976 | Renn et al. | 424/1.1 |
| 4,022,577 | 5/1977 | Brooker et al. | 23/230 B |
| 4,104,026 | 8/1978 | Brooker et al. | 424/1 |
| 4,128,628 | 12/1978 | Brooker et al. | 424/1 |
| 4,248,853 | 12/1981 | Snyder | 424/1 |

OTHER PUBLICATIONS

Chard, T. *An Introduction to Radioimmunoassay and Related Techniques*, North–Holland Pub. Co., Amsterdam 1978.

*Radioimmunoassay of Antibody*, Parrat, D. et al., ed. John Wiley & Sons, Chichester (1982).

*Primary Examiner*—Benjamin R. Padgett
*Assistant Examiner*—M. Moskowitz
*Attorney, Agent, or Firm*—Hamrick, Hoffman, Guillot & Kazubowski

[57] ABSTRACT

An improved radioimmunoassay test method and device based upon competitive binding test methods wherein immunoreactions are halted at a time when the rate of change of the quantity of bound radiolabeled analyte of interest is inversely proportional to the concentration of analyte of interest in an unknown sera. Based thereon, a test device is created having a single calibration curve 36 which is accurate throughout the shelf life of the device.

17 Claims, 5 Drawing Figures

KINETIC RADIOIMMUNOASSAY TEST METHOD AND DEVICE

BACKGROUND OF THE INVENTION

1. Field of the Invention

The present invention relates generally to immunoassay test methods and devices and more particularly to radioimmunoassay test methods and devices.

2. Description of the Prior Art

Many radioimmunoassay test methods and devices have been developed since the pioneering work of Ekins in 1960 and Yalow and Berson in 1960. The standard method for conducting radioimmunoassays, as described by these pioneering researchers, is based upon a theory of competitive binding. Such a test method for a particular antigen of interest, utilizing competitive binding principals, requires an antibody which is specific to the antigen and a quantity of radiolabeled antigen. Liquids containing the unknown antigen and the radiolabeled antigen are reacted with the antibody, and both the unknown antigen molecules and the radiolabeled antigen molecules compete for the binding sites of the antibody molecules. The competitive immunoreaction is conducted until near-equilibrium conditions have been achieved between the bound and unbound reactants. Thereafter, the antibody bound antigen is separated from the liquid reactants by any of several means. Following the separation, the radioactivity of the antibody bound antigen is determined. Further tests are thereafter conducted utilizing a plurality of liquids containing differing known concentrations of the antigen and after equilibrium conditions have been achieved in each of the immunoreactions, the antibody with the bound radioactive antigen from each of such reactions is examined for its radioactivity. Thereafter, a calibration curve is created which correlates the radioactivity from the immunoreactions utilizing known samples with the concentration of antigen in the known samples. Finally, using the calibration curve and the radioactivity of the unknown antigen immunoreaction the concentration of antigen in the unknown sample is determined.

Testing devices, commonly known as test kits, which utilize the above-described competitive binding test method typically contain a quantity of radiolabeled antigen of interest, a quantity of antibody in a form suitable for accomplishing the separation thereof from the liquid reactants, and quantities of each of several different liquids, each having a differing known concentration of the antigen of interest. It is to be realized that due to the slow degradation of the antibody and the decay of the radiolabeled antigen that each time a researcher desires to utilize the test kit, a new calibration curve must be created utilizing each of the several liquids having the differing known concentrations of antigen. Additionally, for each such test, the researcher must conduct the immunoreactions until near-equilibrium conditions exist in the reactions. Such equilibrium conditions typically take thirty minutes or more to be established and some may take up to several days. Thus, immunological testing utilizing the competitive binding test method currently requires a significant amount of time, at least thirty minutes, and the creation of a new calibration curve for each series of test determinations.

SUMMARY OF THE PRESENT INVENTION

It is therefore an object of the present invention to provide a radioimmunoassay test method which does not require near-equilibrium conditions in its immunoreactions, such that it provides rapid results.

It is another object of the present invention to provide a radioimmunoassay test method which does not require the creation of a complete calibration curve in order to provide results.

It is an object of the present invention to provide a radioimmunoassay test kit which contains a single calibration curve which is accurate for the shelf life of the kit.

It is another object of the present invention to provide a radioimmunoassay test kit which is simple and easy to use and produces quick and accurate results.

The instant test method for the quantitative radioimmunoassay of an analyte of interest in endogenous liquid sera utilizes an immunoreagent that is specific to said analyte of interest and which is immobilized on a substrate, and an exogenous liquid containing radiolabeled analyte of interest. The endogenous and exogenous liquids are combined with the immobilized immunoreagent in a reaction vessel and an immunoreaction is permitted to occur. The immunoreaction is halted at a time when the rate of change of the quantity of radiolabeled analyte of interest being bound with said immunoreagent is proportional to the concentration of the analyte of interest in the endogenous liquid. Thereafter, the radioactivity of the immobilized immunoreagent with its bound analyte is determined. Substantially identical test procedures are then performed utilizing liquids containing a zero concentration and other known concentrations of the analyte of interest in place of said endogenous liquid and a calibration curve is created from the results obtained for the known concentration liquids. The test results for the endogenous liquid are then compared with the test results for the known concentration liquids through the use of the calibration curve, and a quantitative determination of the concentration of analyte of interest in the endogenous liquid is completed.

Subsequent tests on further samples of endogenous sera utilize a further substantially identical quantity of the same radiolabeled analyte of interest, more of the zero concentration analyte of interest, a substantially identical immobilized immunoreagent and the calibration curve previously prepared. Such subsequent tests require only the performance of immunoreactions for the unknown endogenous sera and the zero concentration sera. The calibration curve previously prepared is utilized to correlate the results from the two immunoreactions.

The test kit of the instant radioimmunoassay invention includes a plurality of substantially identical immunoreagent coated substrates, a quantity of liquid containing a zero concentration of analyte of interest, a quantity of liquid containing radiolabeled analyte of interest and a calibration curve. The above-described test procedure is conducted for an endogenous liquid containing an unknown concentration of analyte of interest and for the liquid containing a zero concentration of analyte of interest. The results of these two tests are then correlated utilizing the calibration curve and the concentration of analyte of interest in the endogenous liquid is determined. The single calibration curve provided in the test kit is accurate during the shelf life of the kit.

It is an advantage of the radioimmunoassay test method of the present invention that test reactions do not have to be carried out to near-equilibrium conditions, such that results may be quickly and easily obtained.

It is another advantage of the radioimmunoassay test procedure of the present invention that it does not require that a new calibration curve be created for each series of test results.

It is an advantage of the radioimmunoassay test kit of the present invention that a single calibration curve is provided therewith, which calibration curve is accurate throughout the shelf life of the kit.

It is another advantage of the test kit of the present invention that the user thereof need not create a calibration curve for each series of test results which are performed utilizing the kit.

It is a further advantage of the instant invention that a test kit is provided which is simple, quick and easy to use.

These and other objects and advantages of the present invention will no doubt become apparent after reading the following detailed description of the preferred embodiments which are illustrated in the several figures of the drawing.

DESCRIPTION OF THE PREFERRED EMBODIMENT

In conventional quantitative radioimmunoassay (RIA) testing to determine the concentration of a particular analyte of interest in an endogenous serum sample, an immunoreagent, which is specific to the endogenous analyte of interest, is utilized to selectively bind with the endogenous analyte of interest to facilitate its detection and quantitation. The analyte of interest is typically either an antigen or an antibody, and conventional test methods, as well as the instant method, are generally easily modifiable to test for either an antigen or antibody. Throughout the remainder of this application, the description will be that of a test for an antigen of interest. However, it is to be understood that the hereindescribed test method also encompasses a test for an antibody of interest, wherein the word "antigen" would be replaced throughout by "antibody" and the word "antibody" replaced throughout by "antigen."

The conventional RIA test method of interest herein utilizes a competitive binding theory, wherein a known quantity of radioactively tagged exogenous antigen is combined with a known quantity of sera containing an unknown concentration of endogenous antigen in the presence of an antibody which is specific to the antigen. The theory of this test technique is that the endogenous antigen and the tagged exogenous antigen compete for the binding sites of the antibody. The reaction is permitted to proceed to equilibrium whereupon the antibody with its bound antigen (both tagged and untagged) is separated from the liquid reactants and tested for its radioactivity. Concurrently therewith, several substantially identical tests are generally conducted utilizing sera having differing known concentrations of the antigen of interest to create a calibration curve equating radioactivity of the reacted antibody to concentration of antigen. Finally, the concentration of endogenous antigen in the unknown sample is determined by interpolation utilizing the calibration curve and the previously found radioactivity of the reacted antibody for the endogenous antigen.

Conventional wisdom has always taught that it is imperative to achieve near-equilibrium conditions in the competitive binding reaction in order to produce accurate and reproducible results. In that near-equilibrium conditions for immunoreactions having moderate concentrations, on the order of approximately ten through fifty micrograms of antigen per deciliter of liquid, can easily take a half hour or more to achieve, conventional test procedures have typically indicated that the researcher should allow at least forty-five minutes to one hour for the competitive binding reaction, and where any doubt exists, additional reaction time is recommended.

The instant test method also utilizes a competitive binding technique. However, it reports accurate results utilizing reaction times of anywhere from one to ten minutes. It achieves such results by making use of an immunoreaction theory which is different from the equilibrium of reaction theory of conventional competitive binding testing.

The instant test method takes advantage of the immunoreaction theory that in the early stages of a competitive binding immunoreaction, the rate of change of the quantity of radiolabeled antigen bound to the immobilized antibody is inversely proportional to the concentration of endogenous antigen. After approximately 10 minutes, and depending upon the antigen of interest and other reaction parameters, the inverse proportionality relationship begins to change and results from the instant test method tend to become unreliable. However, as speed of testing is often a critical factor in medical treatment, the significant factor of the instant test method is that radioimmunoassay test results can be available in as short a time as one to ten minutes.

The preferred embodiment of the instant method is described as follows with reference to FIG. 1. The initial considerations in testing for a particular endogenous antigen of interest are the selection and preparation of an antibody which is specific to that antigen as well as the preparation of radiolabeled exogenous antigen 10. It is crucial to the instant test method that the antibody be quickly and easily separable from the liquid reactants (sera containing the endogenous antigen and radiolabeled exogenous antigen). To facilitate the separation, the antibody is affixed to a solid substrate, whereby the antibody on the substrate and the liquid reactants may be physically separated in a very rapid manner. In the preferred embodiment, the solid substrate utilized is the inside wall of a test tube, with the antibody being affixed thereto. Such test tubes, with antibody affixed thereto, are commercially available from several suppliers. It is to be noted that the present invention is not to be limited to this substrate as other substrates, such as spherical beads, membranes, or other devices could be substituted therefore. The overriding criteria for the selection of the antibody substrate is that the liquid reactants be separable therefrom in a quick and efficient manner.

With regard to the concentrations and qualities of the liquid reactants that may be effectively utilized in the instant invention, the concentrations and qualities of liquid reactants presently utilized for conventional competitive binding techniques for the various antigens of interest would appear to be quite acceptable. As with conventional competitive binding techniques, the quantities of liquid reactants that are to be utilized in each test must be accurately measured, because the results of the tests for the unknown concentration endogenous sample must be compared with the results of at least one substantially identical concurrent test for a known concentration calibrating sample, in order to make a final determination of the concentration of the antigen in the unknown endogenous sample.

The next step of the instant test method is to initiate the competitive binding reaction of the immobilized antibody with the liquid reactants. This is accomplished by combining the antibody and the liquid reactants within a suitable test vessel 12.

It is important for accurate and reproducible results that both the sera containing the labeled exogenous antigen and the sera containing endogenous antigen be introduced to the antibody on a fixed time interval, preferably simultaneously. Simultaneous introduction of both exogenous and endogenous antigen liquids would minimize any error caused by nonequivalent reaction time from sample to sample.

Various methods might be used to simultaneously combine the two liquid reactants with the immobilized antibody. In the preferred embodiment, simultaneity is achieved by premixing the two liquid reactants together and thereafter introducing the combined reactants to the immobilized antibody. Another method of simultaneously introducing the two reactants to the antibody would be through the use of a dual pipette. Many other methods exist and the instant invention is not to be limited by the means utilized to simultaneously introduce the two liquid reactants to the antibody.

Figure 1:
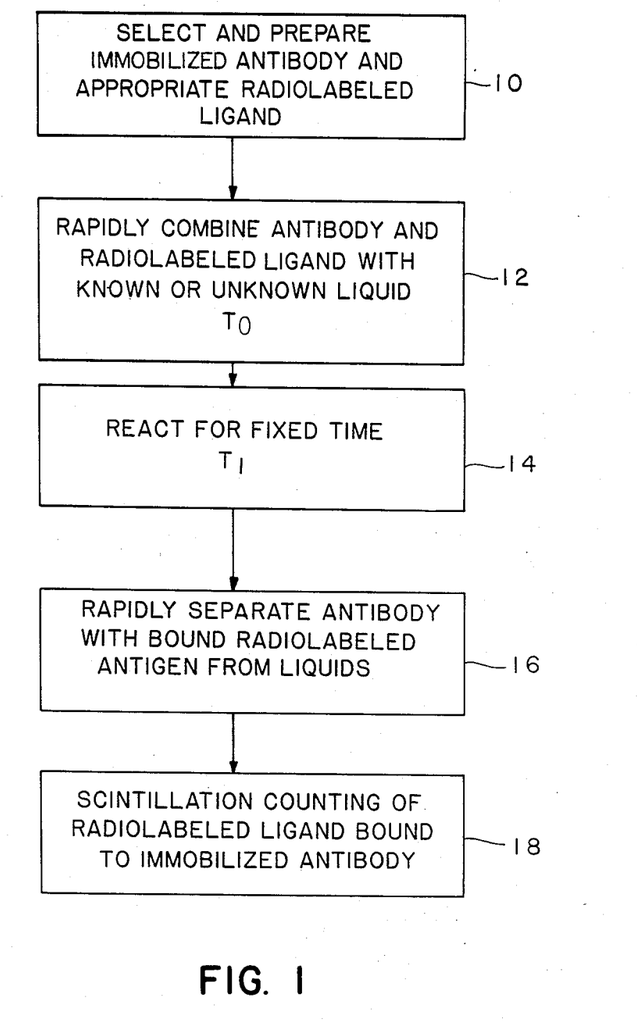
FIG. 1 is a flow chart depicting the radioimmunoassay test method of the present invention.

The reaction is now permitted to proceed for a preselected, fixed period of time 14, shown in FIG. 1 as $T_1$. It is important to note that the calculation of the reaction time $T_1$ commences with time zero $T_0$, at the instant that the reactants are combined with the antibody coated substrate. Significantly, at $T_0$, if the antibody coated substrate were immediately removed from the reaction and placed in a scintillation counter, the number of counts $C_0$ at $T_0$ would be only instrument background counts in that no reaction would have taken place in the first instant of reaction time.

A suitable reaction time ($T_1$) will vary for each type of antigen-antibody reaction. For example, a test for gentamicin could be conducted with a reaction time of as little as approximately three minutes due to the relatively high concentrations of gentamicin in test sera. A test for thyroxine would require a reaction time of approximately five minutes due to the relatively low concentrations of thyroxine in sera. The main criteria in selecting the reaction time for a particular test are that the reaction proceed long enough to obtain meaningful results (longer reaction times being required for antigens having lower concentrations in sera) and that the reaction time be short enough to insure that the inverse proportionality relationship of concentration of endogenous antigen to quantity of radiolabeled antigen bound to the reacted antibody be maintained. Examples provided hereinafter for thyroxine and gentamicin demonstrate reaction times of five minutes and three minutes respectively. However, the present invention is not to be limited to such particular reaction times or such particular reactions.

After the reaction has been permitted to occur for the predetermined reaction time $T_1$ the reaction must be quickly and efficiently halted by the separation of the liquid reactants from the antibody coated substrate 16 with its bound antigen (unlabeled and radiolabeled). The type of separation procedure utilized depends upon the type of antibody coated substrate utilized. For instance, where the antibody coated substrate consists of a test tube which has an antibody coating on its inner wall, separation is achieved by the rapid aspiration of the reactants from the test tube. Where the antibody coating is on spherical beads, membranes or other devices, such devices may be physically removed from the liquid reactants. It is important that the separation be accomplished quickly, within a few seconds of time $T_1$ for example, because the test results for the unknown endogenous antigen sera will be compared to test results for sera of a known antigen concentration which will have undergone a similar test procedure for what should be a substantially identical reaction time.

Following separation from the reactants, the antibody coated substrate is now placed in a scintillation counter 18 to determine the radioactivity (counts per minute) $C_1$ of the antibody coated substrate after reaction time $T_1$.

As has been indicated hereinabove, it is the rate of change of the quantity of radiolabeled antigen bound to the reacted antibody which is inversely proportional to the endogenous antigen concentration for such short reaction times as are utilized in the instant test method. It is to be realized that the rate of change of the quantity of radiolabeled antigen bound to the reacted antibody is measurable by determining the rate of change of radioactivity of the reacted antibody.

The following equation is utilized to determine the rate of change of radioactivity of the reacted antibody from the reaction.

$$(C_1-C_0)/(T_1-T_0)=B \tag{1}$$

In equation 1, B is the rate of change of radioactivity of the reacted antibody in counts per minute, $C_1$ is the radioactivity of the reacted antibody in counts per minute at time $T_1$ (the end of the reaction time), $C_0$ is the counts per minute at time $T_0$ (the starting time of the reaction).

As has been noted hereinabove, the time at $T_0$ is zero seconds and $C_0$ equals only the instrument background counts at time $T_0$. For typical reactions, the background counts may be ignored, thus equating $C_0$ to zero. Thus, because $T_0$ equals zero and $C_0$ equals zero, equation 1 may be simplified to:

$$C_1/T_1=B \tag{2}$$

Equation 2 demonstrates that B may be calculated by taking a single measurement $C_1$ at time $T_1$.

As is typical in conventional competitive binding RIA testing, the results for an unknown sample must be compared with results for known samples to determine the concentration of antigen in the unknown sample. To achieve such a comparison, the instant test method utilizes a calibration curve such as that depicted in FIG. 2. The ordinate of FIG. 2 consists of a relative radioactivity ratio, $B/B_0$. In this ratio, B is the rate of change of radioactivity of the reacted antibody from the unknown sample which has been derived by the test method described hereinabove. $B_0$ is the rate of change of radioactivity of the reacted antibody for a sample known to have a zero concentration of the antigen of interest derived from utilizing the instant test method.

Figure 2:
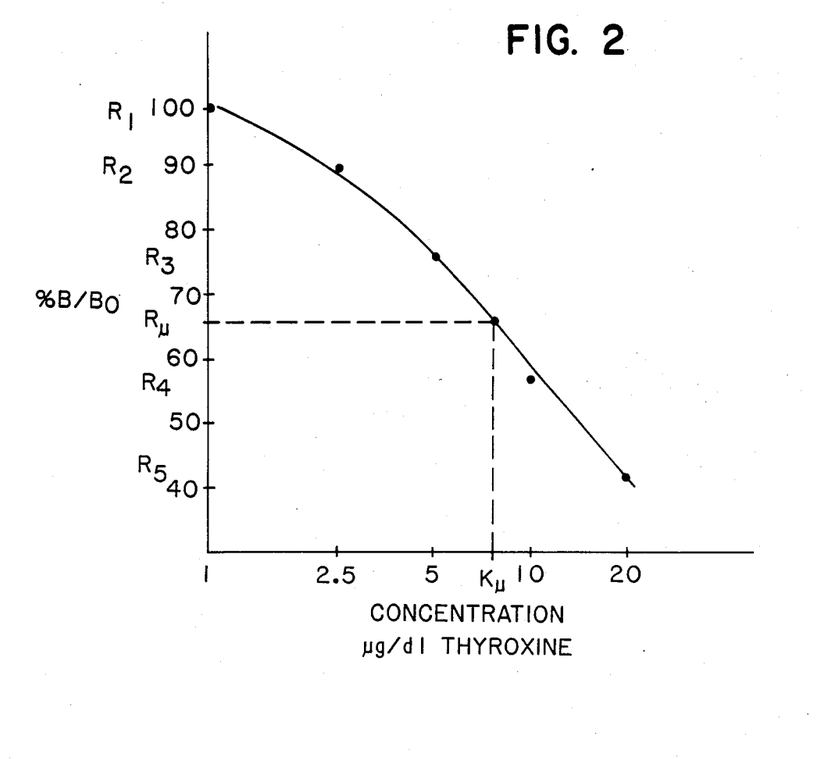
FIG. 2 is a calibration curve of the type utilized in the present test method.

The calibration curve of FIG. 2 is created by conducting several tests utilizing sera having several different known concentrations of the antigen of interest, including a zero concentration, in accordance with the instant test method. To create reliable results, each of the tests for the several sera having known antigen concentrations, as well as each test for an unknown antigen must utilize substantially identical antibody coated substrates, substantially identical quantities of radioactively labeled antigen, substantially identical quantities of test sera and be conducted for substantially identical reaction time.

To aid in the understanding of the instant invention, a test procedure which incorporates the instant test method will now be described through the postulation of a hypothetical testing arrangement which incorporates the instant test method. The hypothetical test arrangement contains nine substantially identical test tubes each of which is substantially identically coated on the inner surface thereof with antibody specific to the antigen of interest. Also postulated are sufficient quantities of six sera, each containing a different known concentration of the antigen of interest; one of the known concentrations is a zero concentration, and the other five known concentrations are sufficiently different from each other to create a calibration curve such as that depicted in FIG. 2. Also postulated is a sufficient quantity of sera containing radioactivity labeled antigen of interest and a sufficient quantity of the endogenous sera containing the unknown concentration of antigen of interest.

Utilizing the above-described test method, a substantially identical quantity of each of the seven different antigen sera (the six knowns and the unknown) are individually premixed with substantially identical quantities of the radioactively labeled antigen. After premixing, each of the seven combined sera are placed in an individual antigen coated test tube and allowed to react for a substantially identical reaction time. At the end of the reaction time the liquid in each of the test tubes is aspirated and each of the test tubes is then individually placed in a scintillation counter for testing. The result from the scintillation counter for each of the known antigen concentrations is each divided by the result for the zero antigen concentration sera to yield the $B/B_0$ relative radioactivity ratio for each of the known concentration sera, these ratios being $R_1$, $R_2$, $R_3$, $R_4$, and $R_5$, as shown in FIG. 2. These ratios are then utilized with the known concentrations of the samples that were used to determine them to create a calibration curve such as that depicted in FIG. 2.

The result from the scintillation counter for the unknown endogenous serum sample is likewise divided by the result for the zero concentration sample to yield a relative radioactivity ratio $R_u$. This ratio is utilized in conjunction with the calibration curve of FIG. 2 to yield the concentration ($K_u$) of antigen in the unknown endogenous serum sample. Of course, more than one unknown sample could be tested at this time provided there were sufficient antibody coated test tubes and radiolabeled antigen to do so.

A significant advantage of the instant test method is realized when an additional test for an unknown concentration serum sample is to be conducted perhaps a week or a month after the initial tests described hereinabove. It has been found that although the radioactivity of the remaining radioactively tagged antibody may have decayed, that the calibration curve previously created is still accurate and utilizable. Thus, to conduct such a later test for a second unknown, it is only required that two new test results be obtained, one for the sera having the known zero concentration of antigen of interest and one for the second unknown serum. To obtain such results, the test method is repeated utilizing the eighth and ninth test tubes, the radioactively labeled antigen which was utilized in creating the calibration curve and an identical reaction time. The result from the scintillation counter for the unknown endogenous sera is divided by the new result for the zero concentration sera and, utilizing the calibration curve, the concentration of antigen of interest in the second unknown endogenous sera is derived.

Figure 3:
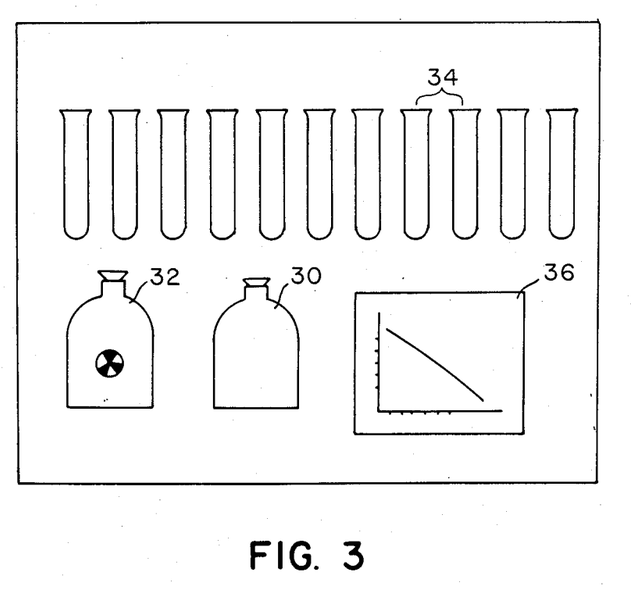
FIG. 3 is a schematic diagram of a test kit of the instant invention.

The significance of the constancy of the calibration curve is realized in the manufacture and marketing of test kits utilizing the instant test method. Prior to shipment, a manufacturer can create a constant calibration curve for the antibody coated substrates, zero antigen concentration sera and radioactively labeled antigen which will be included in the test kit. The test kit, see FIG. 3, as shipped to the customer, will then only require sufficient quantities of zero antigen concentration sera 30, radioactively labeled antigen 32, a sufficient quantity of substantially identical antibody coated substrates 34 and a single calibration curve 36. The customer need never create his own calibration curve for tests conducted during the shelf life of the test kit. Each time the customer desires to utilize the test kit, he need only determine the value $B_0$ for the zero concentration antigen sera in addition to the values B (see equation 2) for each of the unknown endogenous sera that are being tested. Thus, while the value $B_0$ will decrease during the shelf life of the test kit, due to decay of radioactivity, the calibration curve, which utilizes the relative radioactivity ratio $B/B_0$, will not change during the shelf life of the test kit. This is a significant advantage over existing RIA competitive binding test kits in that such existing test kits require the derivation of a complete calibration curve each time testing is conducted.

The basic reason why a new calibration curve must be created with existing RIA competitive binding procedures is because such test procedures utilize the long reaction times necessary to achieve near-equilibrium conditions of the immunoreactions. These equilibrium conditions change during the shelf life of the existing test kit and thus the calibration curve also changes. The instant test method specifically avoids equilibrium conditions and instead produces accurate results from the very early stages of the immunoreaction when non-equilibrium conditions exist. It is to be observed that after equilibrium conditions have been achieved in a competitive binding immunoreaction, that the rate of change of radioactivity of the reacted antibody is zero and the instant test procedure would be meaningless. Because the instant test method makes use of non-equilibrium immunoreaction phenomena, it is significantly different in both theory and practice from the preexisting RIA competitive binding test procedures.

The instant test method is widely applicable to RIA testing of antigens and antibodies. It will be exemplified by particular examples of tests conducted for thyroxine (T4) and gentamicin. However, the instant test method is not to be restricted to such particular examples.

EXAMPLE I

Kinetic Radioimmunoassay For Thyroxine (T4)

A test for thyroxine (T4) was conducted wherein the specific antibody is rabbit anti-thyroxine (anti-T4), the antigen is thyroxine (T4) and the radiolabeled antigen is iodine 125 labeled thyroxine ($^{125}$I-T4).

In the kinetic radioimmunoassay for thyroxine, the specific antibody was formed by injecting New Zealand white rabbits with a thyroxine-bovine serum albumin conjugate. The specific antiserum obtained subsequently was then fractionated to isolate the immunoglobulin G (IgG) fraction. The IgG fraction, which acts as the antibody, was then immobilized onto the internal surface of test tubes of water-insoluble material. The radiolabeled T4 was prepared by a modified procedure of Hunter and Greenwood, as described in *Nature,* Vol. 194, Page 495, published in 1962). Other well known methods of preparation could be substituted therefor.

The kinetic radioimmunoassay for T4 was then conducted by introducing 20 microliters of unknown concentration serum sample and 1 ml of $^{125}$I-T4 tracer solution into an anti-T4 coated test tube. The reaction mixture was quickly aspirated after five minutes of incubation. The radioactivity of the test tube was determined in a gamma counter with the window suitably adjusted for iodine 125. Similar test procedures were then conducted for several samples, having differing known concentrations, including a zero concentration sample. The relative radioactivity ratios ($B/B_0$) of the several known standards to the reference zero standard were determined and plotted along the ordinate against the known T4 concentration along the abscissa to form a calibration curve such as is shown in FIG. 2. The T4 concentration in the unknown sample was then determined by interpolation from the curve.

EXAMPLE IA

Sensitivity Of The Kinetic Radioimmunoassay For Thyroxine (T4)

In further testing, the sensitivity of the instant test method, defined as the smallest amount of thyroxine which can be distinguished from zero thyroxine concentration with 95% confidence, was found to be 1.6 μg/dl.

EXAMPLE IB

Reproducibility Of The Kinetic Radioimmunoassay For Thyroxine (T4)

"Within Day" precision and "Day to Day" precision were determined for the instant test method. The values determined for thyroxine at low, midrange, and high levels are presented in Tables 1 and 2.

TABLE 1

| With Day Precision (n = 20) | | |
|---|---|---|
| Mean (μg/dl) | S.D. (μg/dl) | C.V. (%) |
| 5.3 | 0.47 | 8.9 |
| 9.8 | 0.68 | 6.9 |

TABLE 1-continued

| With Day Precision (n = 20) | | |
|---|---|---|
| Mean (μg/dl) | S.D. (μg/dl) | C.V. (%) |
| 14.7 | 1.32 | 9.0 |

TABLE 2

| Day to Day Precision (n = 12) | | |
|---|---|---|
| Mean (μg/dl) | S.D. (μg/dl) | C.V. (%) |
| 4.6 | 0.33 | 7.2 |
| 6.8 | 0.38 | 5.6 |
| 13.0 | 0.74 | 5.7 |

EXAMPLE IC

Figure 4:
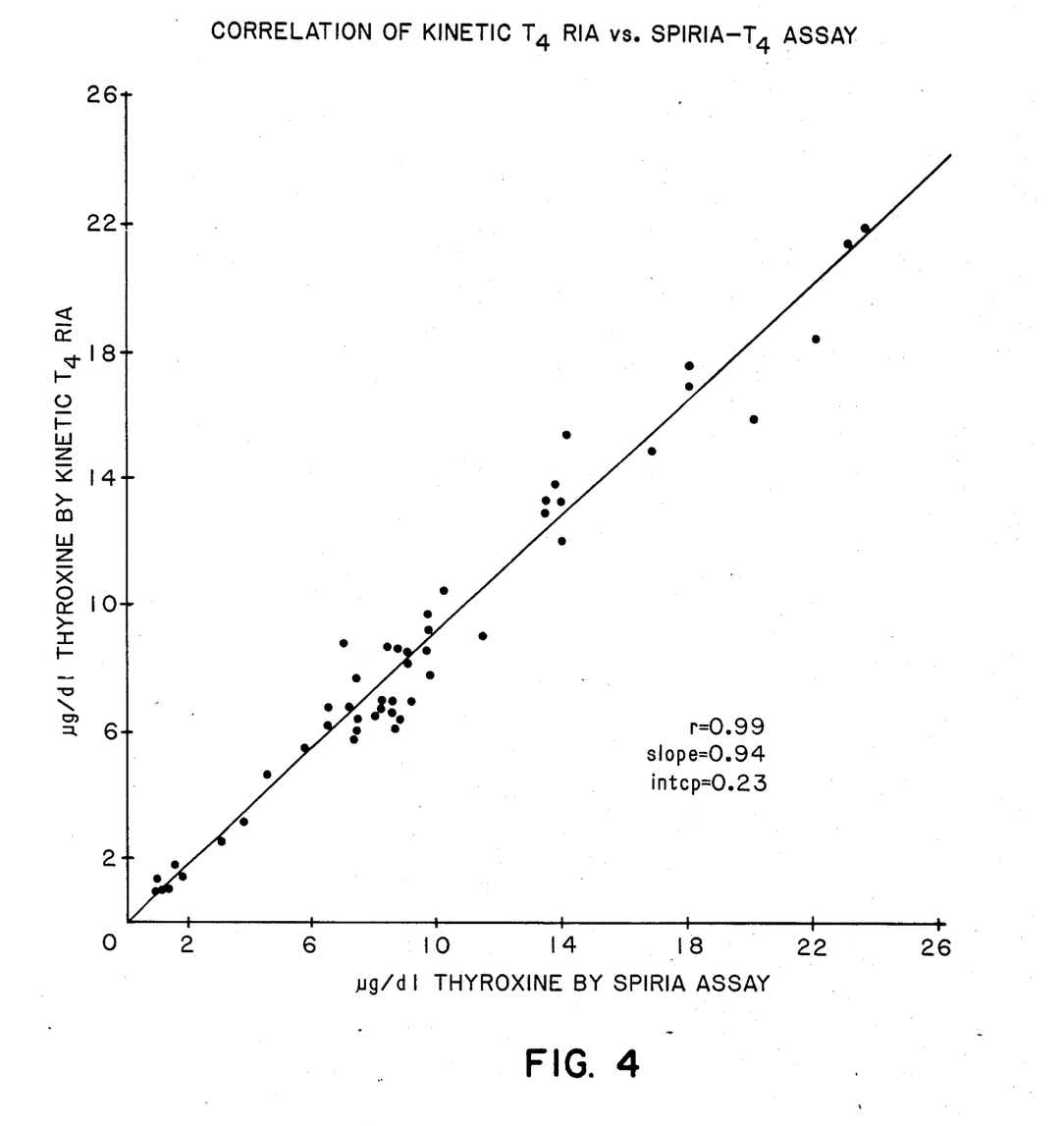
FIG. 4 is a correlation curve comparing the results of the instant test method with results from another solid-phase test method for thyroxine.

Correlation Of The Results Of The Kinetic Radioimmunoassay For Thyroxine (T4) With A Solid-Phase Thyroxine (T4) Radioimmunoassay The accuracy of the instant test method for thyroxine T4 was determined by comparing quantitation of clinical patients T4 serum samples by this procedure with quantitation determined by an independent solid-phase RIA procedure. As is depicted in FIG. 4, an excellent correlation (r=0.99) was obtained between these two procedures.

EXAMPLE II

Kinetic Radioimmunoassay for Gentamicin

A test for gentamicin was conducted wherein the specific antibody is rabbit anti-gentamicin, the antigen is gentamicin and the radiolabeled antigen is iodine 125 labeled gentamicin.

In the kinetic radioimmunoassay for gentamicin, the specific antibody was formed by injecting New Zealand white rabbits with a gentamicin-bovine serum albumin conjugate. The specific antiserum obtained subsequently was then fractionated to isolate the immunoglobulin G (IgG) fraction. The IgG fraction, which acts as the antibody, was then immobilized onto the internal surface of a test tube of water-insoluble material. The radiolabeled gentamicin was prepared by a modified procedure of Hunter and Greenwood, as described in *Nature,* Vol. 194, Page 495, published in 1962. Other well known methods for preparation could be substituted therefor.

Figure 5:
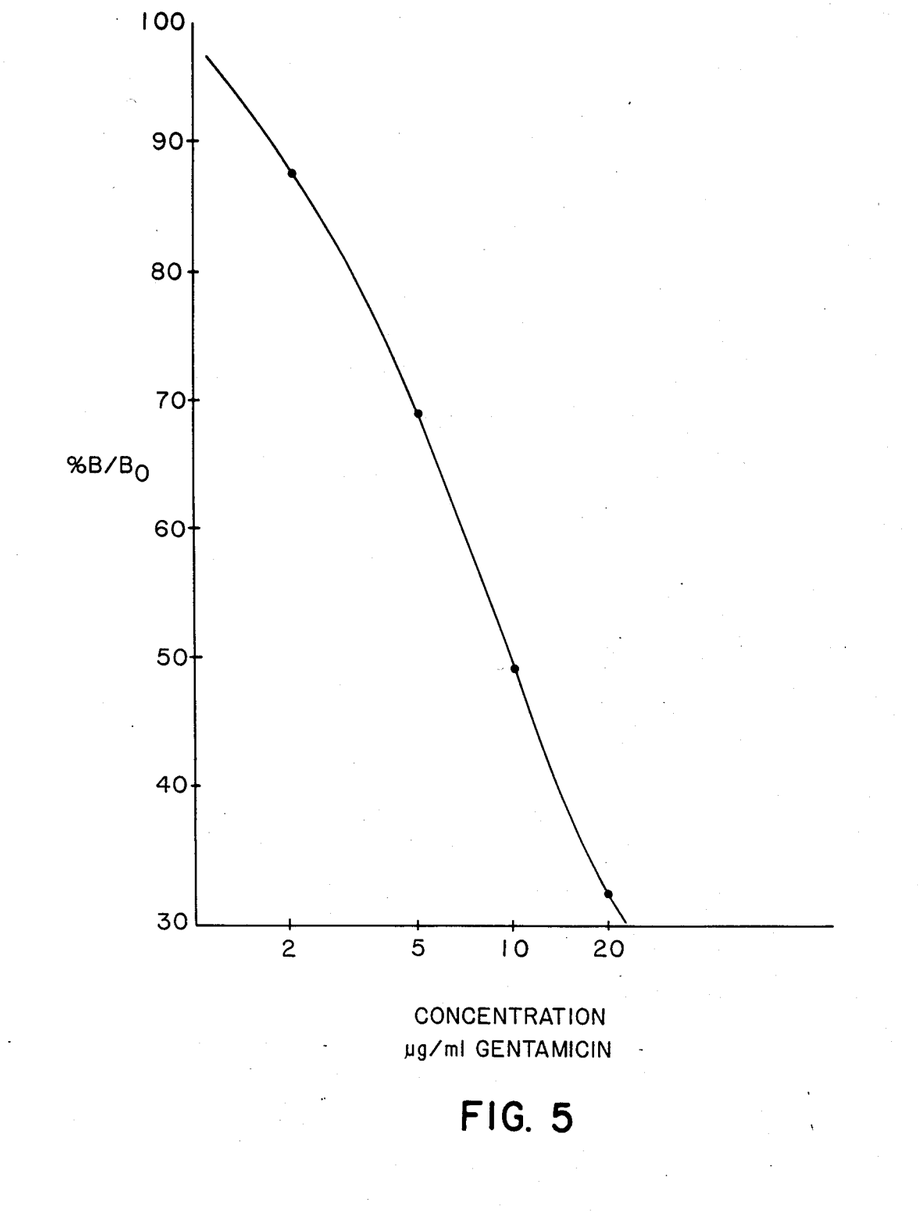
FIG. 5 is a calibration curve created for a test for gentamicin.

The kinetic radioimmunoassay for gentamicin was then conducted by introducing 50 microliters of a 1:100 PBS prediluted serum sample and 1 ml of 125I-gentamicin tracer solution into an anti-gentamicin coated test tube. The reaction mixture was quickly aspirated after three minutes of incubation. The radioactivity of the test tube was determined in a gamma counter with the window suitably adjusted for iodine 125. Similar test procedures were then conducted for several samples having differing known concentrations, including a zero concentration sample. The relative radioactivity ratios ($B/B_0$) of the several known standards to the reference zero standard were determined and plotted along the ordinate against the known gentamicin concentration along the abscissa to form a calibration curve such as is shown in FIG. 5. The gentamicin concentration in the unknown sample was then determined by interpolation from the curve.

While the instant test method and test kit have been particularly shown and described with reference to certain embodiments, it will be understood by those skilled in the art that various alterations and modifications in form and detail may be made therein. Accordingly, it is intended that the following claims cover all such alterations and modifications as fall within the true spirit and scope of the invention.

What is claimed is:

1. A test method for the quantitative radioimmunoassay of an analyte of interest in endogenous liquid sera utilizing an immunoreagent that is specific to said analyte of interest, which immunoreagent is immobilized on a substrate, and an exogenous liquid containing radiolabeled analyte of interest, comprising the steps of:
   (a) combining a measured volume of said endogenous liquid and a measured volume of said exogenous liquid with said immobilized immunoreagent in a reaction vessel and permitting an immunoreaction to occur;
   (b) separating the immobilized immunoreagent from said liquids prior to equilibrium conditions being reached in said immunoreaction;
   (c) obtaining a test result by making a quantitative determination of the rate of change of the quantity of said radiolabeled analyte bound to said immobilized immunoreagent;
   (d) repeating the above-described steps (a), (b) and (c) utilizing a calibrating liquid containing a concentration of a standard amount of said analyte of interest in place of said endogenous liquid, the volume of said calibration liquid being substantially identical to said measured volume of endogenous liquid;
   (e) comparing the result of the instant test method for said endogenous liquid having an unknown concentration of said analyte of interest with said test result of the instant test method for said calibrating liquid to produce a quantitative determination of the concentration of said analyte of interest in said endogenous liquid.

2. A test method for the quantitative radioimmunoassay of an analyte of interest in endogenous liquid sera utilizing an immunoreagent that is specific to said analyte of interest, which immunoreagent is immobilized on a substrate, and an exogenous liquid containing radiolabeled analyte of interest, comprising the steps of:
   (a) combining a measured volume of said endogenous liquid and a measured volume of said exogenous liquid with said immobilized immunoreagent in a reaction vessel and permitting an immunoreaction to occur;
   (b) separating the immobilized immunoreagent from said liquids at a time when the rate of change of the quantity of said radiolabeled analyte of interest bound with said immunoreagent in the immunoreaction is inversely proportional to the concentration of said analyte of interest in said endogenous liquid;
   (c) obtaining a test result by making a quantitative determination of the rate of change of the quantity of said radiolabeled analyte bound to said immobilized immunoreagent;
   (d) repeating the above-described steps (a), (b) and (c) utilizing a calibrating liquid containing a concentration of a standard amount of said analyte of interest in place of said endogenous liquid, the volume of said calibrating liquid being substantially identical to said measured volume of endogenous liquid;
   (e) comparing the test result of the instant test method for said endogenous liquid having an unknown concentration of said analyte of interest with said test result of the instant test method for said calibrating liquid to produce a quantitative determination of the concentration of said analyte of interest in said endogenous liquid.

3. A test method as described in claims 1 or 2 wherein said endogenous and exogenous liquids are simultaneously combined with said immobilized immunoreagent.

4. A test method as described in claims 1 or 2 wherein said analyte of interest is an antigen and said immunoreagent is an antibody which is specific to said antigen.

5. A test method as described in claims 1 or 2 wherein said separation described in subpart (b) is conducted at a time of from one to 10 minutes after the combining of said liquids with said immobilized immunoreagant.

6. A test method as described in claims 1 or 2 wherein said immunoreagent is immobilized on an inside wall of said reaction vessel.

7. A test method for the quantitaradioimmunoassay of an antigen of interest in endogenous liquid sera utilizing an immobilized antibody that is specific to said antigen of interest and an exogenous liquid containing radiolabeled antigen of interest, comprising the steps of:
   (a) simultaneously combining a measured volume of said endogenous liquid with a measured volume of said exogenous liquid in a reaction vessel having said antibody immobilized on an inner surface thereof, and permitting an immunoreaction to occur;
   (b) aspirating said liquids from within said vessel at a time when the rate of change of the quantity of said radiolabeled antigen of interest bound to said antibody in said immunoreaction is inversely proportional to the concentration of said antigen in said endogenous liquid sera;
   (c) obtaining a test result by determining the rate of change of the quantity of said radiolabeled antigen bound to said antibody;
   (d) repeating the above-described steps (a), (b) and (c) utilizing a calibrating liquid having a zero concentration of said antigen of interest in place of said endogenous liquid, the volume of said calibrating liquid being substantially identical to said measured volume of endogenous liquid;
   (e) repeating the above-described steps (a), (b) and (c) for each of a plurality of calibrating liquids, each containing differing concentrations of a standard amount of said antigen of interest in place of said endogenous liquid, the volume of each said calibrating liquid being substantially identical to said measured volume of endogenous liquid;
   (f) creating a calibration curve which correlates the concentrations of antigen of interest in each of said plurality of calibrating liquids with a relative radioactivity ratio derived by dividing the test result obtained for each of said calibrating liquids by the test result obtained for said zero concentration calibrating liquid;
   (g) calculating a relative radioactivity ratio for said endogenous liquid by dividing the test result of said endogenous liquid by the test result for said zero concentration liquid; and
   (h) making a determination of the concentration of antigen of interest in said endogenous liquid utilizing the calibration curve described in sub-part (f) hereinabove and the ratio described in sub-part (g) hereinabove.

8. A test method as described in claim 7 wherein said aspiration described in subpart (b) is conducted at a time of from one to ten minutes after the combining of said liquids with said immobilized antibody.

9. A test method for the quantitative radioimmunoassay of an analyte of interest in endogenous liquid sera utilizing an immunoreagent that is specific to said analyte of interst, which immunoreagent is immobilized on substrate, and an exogenous liquid containing radiolabeled analyte of interest, comprising the steps of:
   (a) combining a measured volume of said endogenuos liquid and measured volume of said exogenous liquid with said immobilized immunoreagent in a vessel and permitting an immunoreaction to occur;
   (b) determining the rate of changes of the quantity of radiolabeled analyte of interest that is bound to said immunoreagent at a time when the rate of change of the quantity of bound radiolabeled analyte of interest is inversely porportional to the concentration of analyte of interest in said endogenous liquid;
   (c) comparing the results of sub-part (b) with the results of steps (a) and (b) of the instant test procedure when conducted utilizing at least one calibrating liquid having a concentration of a standard amount of said analyte of interest in place of said endogenous liquid, the volume of said calibrating liquid being substantially identical to said measured volume of endogenous liquid, whereby the concentration of analyte of interest in the endogenous liquid is determined.

10. A test method for the quantitative radioimmunoassay of an analyte of interest in endogenous liquid sera utilizing competitive binding test procedures wherein the rate of change of the quantity of radiolabeled analyte of interest bound to an immunoreagent in an immunoreaction is determined at a time when said rate of change of the quantity of bound radiolabeled analyte of interest is inversely proportional to the concentration of analyte of interest in said endogenous liquid, said rate of change being utilized to determine the concentration of analyte of interest in said endogenous liquid sera.

11. A test method for the quantitative radioimmunoassay of an analyte of interest in endogenous liquid sera utilizing an immunoreagent that is specific to said analyte of interest, which immunoreagent is immobilized on a substrate, and an exogenous liquid containing radiolabeled analyte of interest, comprising the steps of:
   (a) combining a measured volume of said endogenous liquid and a measured volume of said exogenous liquid with said immobilized immunoreagent in a reaction vessel and permitting an immunoreaction to occur:
   (b) determining the rate of change of the quantity of radiolabeled analyte of interest which is bound to said immobilized immunoreagent at a time prior to equilibrium conditions being reached in said immunoreaction;
   (c) repeating the above-described steps (a) and (b) utilizing a calibrating liquid containing a concentration of a standard amount of said analyte of interest in place of said endogenous liquid, the volume of said calibrating liquid being substantially identical to said measured volume of endogenous liquid;
   (d) comparing the result of the instant test method for said endogenous liquid having an unknown concentration of said analyte of interest with said test result of the instant test method for said calibrating liquid to produce a quantitative determination of the concentration of said analyte of interest in said endogenous liquid.

12. A test method for the quantitative radioimmunoassay of an analyte of interest in endogeous liquid sera utilizing an immunoreagent that is specific to said analyte of interest, which immunoreagent is immobilized on a substrate, and an exogenous liquid containing radiolabeled analyte of interest, comprising the steps of:
   (a) combining a measured volume of said endogenous liquid and a measured volume of said exogenous liquid with said immobilized immunoreagent in a reaction vessel and permitting an immunoreaction to occur;
   (b) determing the rate of change of the quantity of radiolabeled analyte of interest which is bound to said immobilized immunoreagent at a time when said rate of change is inversely proportional to the concentration of said analyte of interest in said endogenous liquid;
   (c) repeating the above-described steps (a) and (b) utilizing a calibrating liquid containing a concentration of a standard amount of said analyte of interest in place of said endogenous liquid, the volume of said calibrating liquid being substantially identical to said measured volume of endogenous liquid;
   (d) comparing the result of the instant test method for said endogenous liquid having an unknown concentration of said analyte of interest with said test result of the instant test method for said calibrating liquid to produce a quantitative determination of the concentration of said analyte of interest in said endogenous liquid.

13. A test method as described in claims 11 or 12 wherein said determination described in step (b) involves the measurement of the quantity of radiolabeled analyte of interest which is bound to said immobilized immunoreagent at least two different times.

14. A test method as described in claim 13 wherein a first said measurement $(C_o)$ is taken at a first time $(T_o)$ and a second said measurement $(C_1)$ is taken at a second time $(T_1)$ and said rate of change (B) of the quantity of radiolabeled analyte of interest bound to said immobilized immunoreagent is determined mined utilizing the formula $B=(C_1-C_o)/(T_1-T_o)$.

15. A test method as described in claim 14 wherein said endogenous and exogenous liquids are simultaneously combined with said immobilized immunoreagent.

16. A test method as described in claim 14 wherein said analyte of interest is an antigen and said immunoreagent is an antibody which is specific to said antigen.

17. A test method as described in claim 14 wherein said first and second measurements are conducted at a time of from one to ten minutes after the combining of said liquid with said immobilized immunoreagent.

* * * * *